US006103275A

United States Patent [19]
Seitz et al.

[11] Patent Number: 6,103,275
[45] Date of Patent: Aug. 15, 2000

[54] SYSTEMS AND METHODS FOR TOPICAL TREATMENT WITH NITRIC OXIDE

[75] Inventors: William A. Seitz, Dickinson; Robert E. Garfield, Friendswood, both of Tex.; Alexandru T. Balaban, Columbia, Md.; Randall J. Stewart, Galveston, Tex.

[73] Assignee: Nitric Oxide Solutions, Dickinson, Tex.

[21] Appl. No.: 09/095,174

[22] Filed: Jun. 10, 1998

[51] Int. Cl.$^7$ .................................................. A61K 33/00
[52] U.S. Cl. ............................................................ 424/718
[58] Field of Search ............................................. 424/718

[56] References Cited

U.S. PATENT DOCUMENTS

| | | |
|---|---|---|
| 3,813,249 | 5/1974 | Ezekiel et al. . |
| 4,535,154 | 8/1985 | Keefer et al. . |
| 4,954,526 | 9/1990 | Keefer . |
| 5,039,705 | 8/1991 | Keefer et al. . |
| 5,155,137 | 10/1992 | Keefer et al. . |
| 5,185,376 | 2/1993 | Diodati et al. . |
| 5,208,233 | 5/1993 | Keefer et al. . |
| 5,212,204 | 5/1993 | Keefer et al. . |
| 5,250,550 | 10/1993 | Keefer et al. . |
| 5,498,421 | 3/1996 | Grinstaff et al. . |
| 5,519,020 | 5/1996 | Smith et al. ............................ 424/718 |
| 5,648,101 | 7/1997 | Tawashi ................................. 424/718 |
| 5,683,668 | 11/1997 | Hrabie et al. .......................... 423/405 |
| 5,698,738 | 12/1997 | Garfield et al. . |
| 5,789,447 | 8/1998 | Wink et al. ............................ 514/611 |
| 5,840,759 | 11/1998 | Mitchell et al. ....................... 514/610 |
| 5,888,528 | 3/1999 | Wellinghoff et al. ................. 424/405 |

FOREIGN PATENT DOCUMENTS

| | | |
|---|---|---|
| 2054661 | 5/1972 | Germany . |
| WO 96/40058 | 12/1996 | WIPO . |

OTHER PUBLICATIONS

Abdalla et al., "Prevention of Bone Mineral Loss is Postmenopausal Women by Norethisterone", *Obstetrics and Gynecology,* vol. 66, No. 6, pp. 789–792, 1985.

Ahokas et al., "Enhanced Endothelium–Derived Relaxing Factor Activity in Pregnant Spontaneously Hypersensitive Rats," *Am. J. Obstet. Gynecol.* (Abstract), 164(1):242, 1991.

Alam et al., "A Hypothesis for the Local Control of Osteoclast Function by Ca$^{2+,}$ Nitric Oxide and Free Radicals,", *Bioscience Reports,* vol. 12, No. 5, pp. 369–380, 1992.

Balaban and Istratoiu, "N–Arenesulphonyl–N–(2,2,6, 6–Teramethylpiperidyl–1)–Aminyls, Hydrazyls with No Nitrogen–Bonded Aromatic Groups," *Tetrahedron Letters,* 21:1879–80, 1973.

Balaban and Negotia, "Factors Affecting Stability and Equilibria of Free Radicals. VII Arenesulphonyl–Phenyl–Nitroxides and 1–Anenesulphonyl–2,2–Diphenylhydrazyls," *Revue Roumaine de Chimie,* 17(7):1227–34, 1972.

Balaban et al., "Aryl–N–nitroso Nitroxides," *Journal of Magnetic Resonance,* 9:1–7,1973.

Balban et al., "Model MNDO Calculations for Rotamers of α–Acylnitroxides and of N–Nitrosonitroxides," *Tetrahedron,* 43(2):405–08, 1987.

Balban et al., "N–Nitroso–Phenyl–Nitroxide," *Revue Roumaine de Chimie,* 16(5):721–23, 1971.

Clark and Shaw, "Stable emulsions of highly fluorinated organic compounds for preparation of artificial blood formulations", *Chemical Abstracts,* vol. 107:242588t, 1987.

Clark, Leland and Gollan, "Survival of Mammals Breathing Organic Liquid Equilibriated with Oxygen at Atmospheric Pressure", *Science,* vol. 152, pp. 1755–1756, 1966.

Culotta and Koshland, Jr., "No News is Good News," *Science,* 258:1862–65, 1992.

Diodati et al., "Complexes of Nitric Oxide with Nucleophiles as Agents for the Controlled Biological Release of Nitric Oxide: Hemodynamic Effect in the Rabbit," *Journal of Cardiovascular Pharmacology,* 22:287–92, 1993.

Drago and Karstetter, "The Reaction of Nitrogen(II) Oxide with Various Primary and Secondary Amines," *J. Am. Chem. Soc.,* 83:1819–22, 1961.

Drago et al., "A Mechanism for the Reaction of Diethylamine with Nitric Oxide," *J. Am. Chem. Soc.,* 83:4337–39, 1961.

Drago, "Reactions of Nitrogen(II) Oxide," *Amer. Chem. Soc.,* Ch. 15, pp. 143–149, 1962.

Erner, "Preparation of fluorinated triethylenediamines for an oxygen transport agent and blood–substitute emulsion containing them", *Chemical Abstracts,* vol. 113:138569a, No. 16, 1990.

Feelisch and Stamler, "Donors of nitrogen oxide," In: Methods in Nitric Oxide Research, Wiley, New York, pp. 71–115, 1996.

Feelisch, "Biotransformation to nitric oxide of organic nitrates in comparison to other nitrovasodilators," *European Heart Journal,* 14(Supp.I):123–32, 1993.

(List continued on next page.)

*Primary Examiner*—James H. Reamer
*Attorney, Agent, or Firm*—Daniel S. Hodgins

[57] ABSTRACT

A simple, biocompatible system and procedure for generating nitric oxide (NO) is described. A mixture of powdered sodium nitrite, ascorbic acid, and maleic acid (or another organic acid of adequate strength) immediately generates nitric oxide (NO) on treatment with water. To slow down the NO generation, one may prepare an ointment from a nonaqueous medium (petrolatum, vaseline) and the three powdered ingredients, which on being applied topically on the skin will release NO as water permeates through this medium; alternatively, one may convert the aqueous sodium nitrite solution into a gel with hydroxyethylcellulose (or other gel-forming compound) and combine this gel with another gel obtained from aqueous ascorbic and maleic acids with hydroxyethylcellulose for topical application (on intact skin, burns, intra-cavity, etc.). The two gels may be admixed immediately before use (possibly from a single container with separate chambers and dual nozzle, via pushing or squeezing the two gels through the nozzle), or may be applied in sandwich-like fashion (possibly as a transdermal patch) for further slowing down the delivery of NO.

19 Claims, 7 Drawing Sheets

OTHER PUBLICATIONS

Feelisch, "The Biochemical Pathways of Nitric Oxide Formation from Nitrovasodilators: Appropriate Choice of Exogenous No Donors and Aspects of Preparation and Handling of Aqueous No Solutions," *Journal of Cardiovascular Pharmacology,* 17(Suppl. 3):S25–S33, 1991.

Furchgott and Zawadzki, "The obligatory role of endothelial cells in the relaxation of arterial smooth muscle by acetylcholine," *Nature,* 288:373–76, 1980.

Geyer, "Fluorocarbon–Polyol Artificial Blood Substitutes", *Seminars in Medicine of the Beth Israel Hospital, Boston,* vol. 289, No. 20, pp. 1077–1082, 1973.

Hansen, Croisy, Keefer, "N–Nitrosation of Secondary Amines by Nitric Oxide Via the 'Drago Complex'," *In: N–Nitroso Compounds: Occurrence and Biological Effects,* Bartsch et al., Eds., National Cancer Institute, Bethesda, MD, International Agency for Research on Cancer Publication No. 41, pp. 21–29, 1992.

Ignarro, "Signal Transduction Mechanisms Involving Nitric Oxide," *Biochemical Pharmacology,* 41(4):485–90, 1991.

Iida et al., "Reactions of nitrosobenzenes with nitrogen monoxide," *Chemistry Abstracts,* The American Chemical Society, 89(21):573, Abstract No. 179627x, 1978.

Isono et al., "Effect of FK409, a Novel Nitric Oxide Donor, on Acute Experimental Myocardial Ischemia," *Japan. J. Pharmacol.,* 62:315–24, 1993.

Izumi et al., "Gestational changes in L–arginine–induced relaxation of pregnant rat and human myometrial smooth muscle," *Am. J. Obstet. Gynecol.,* 169(5):1327–37, 1993.

Kamm and Marvel, "B–Phenylhydroxylamine (Hydroxylamine, N–phenyl–)$C_6H_5NO_2$+2Zn+2ZnO," *Org. Synth. Coll.,* 8(1):445–47, 1941.

Kasten et al., "Potentiation of osteoclast bone–resorption activity by inhibition of nitric oxide synthase," *Proc. Natl. Acad. Sci. USA,* 91:3569–73, 1994.

Kaufman and Richard, "Emulsions of highly fluorinated organic compounds as blood substitutes" *Chemical Abstracts,* vol. 113:46356a, 1990.

Keefer et al., "Chemistry of the NONOates", In:*Nitrosamines and Related N–Nitroso Compounds,* 204th National Meeting of the American Chemical Society, ACS Symposium Series 553, Loeppky, C. Midhejda, Eds., Ch. 11, pp. 136–146, 1994.

Keefer, "N–oxy–N–nitrosamine derivatives their preparation, and their use as antihypertensives," *Chemical Abstracts,* The American Chemical Society, 113(17):71, Abstract No. 1453446, 1990.

Keefer et al., "'NONOates' (1–substituted diazen–1–ium–1, 2–diolates) as nitric oxide donors: convenient nitric oxide dosage forms," *Methods in Enzymology,* 268:281–293, 1996.

Knowles and Moncada, "Nitric oxide as a signal in blood vessels," *TIBS,* 17:399–402, 1992.

Koshland, Jr., "The Molecule of the Year," *Science,* 258:1861, 1992.

Lees et al., "Arrest of preterm labour and prolongation of gestation with glyceryl trinitrate, a nitric oxide donor," *The Lancet,* 343:1325–26, 1994.

Longhi et al., "Reactions of Nitrogen(II) Oxide with Miscellaneous Lewis Bases," *Inorganic Chemistry,* 1(4):768–70, 1962.

Lowik et al., "Inducible Production of Nitric Oxide in Osteoblast–like Cells and in Fetal Mouse Bone Explants Is Associated with Suppression of Osteoclastic Bone Resorption", *J. Clin. Invest.,* vol. 93, pp. 1465–1472, 1994.

MacIntyre et al., "Osteoclastic inhibition: An action of nitric oxide not mediated by cyclic GMP", *Proc. Natl. Acad. Sci. USA,* vol. 88, pp. 2936–2940, 1991.

Maragos et al., "Complexes of No with Nucleophiles as Agents for the Controlled Biological Release of Nitric Oxide. Vaso relaxant Effects," Abstract, MED, Abstract No. 63.

Marvel and Kamm, "Cupferron," *Org. Synth. Coll.,* 8(1):177–79, 1941.

Minisci and Galli, "Communicazioni brevi," *Chimica e Industria (Milano),* 46:423, 1964.

Molnar and Hertelendy, "Nω–Nitro–L–arginine, an inhibitor of nitric oxide synthesis, increases blood pressure in rats and reverses the pregnancy–induced refractoriness to vasopressor agents", *Am J Obstet Gynecol,* vol. 166, No. 5, pp. 1560–1567, 1992.

Moncada et al., "Nitric Oxide: Physiology, Pathophysiology, and Pharmacology," *Pharmacological Reviews,* 43(2):109–42, 1991.

Negoita et al., "N–(2,4,6–Tricarbomethoxyphenyl)–Alkoxyaminyls, New Push–Pull Stable Nitrogen Free Radicals," *Tetrahedron Letters,* 21:1877–78, 1973.

Pinto et al., "Endothelial–derived relaxing factor released by endothelial cells of human umbilical vessles and its impairment in pregnancy–induced hypertension," *Am. J. Obstet. Gynecol.,* 164(2):507–13, 1991.

Ragsdale et al., "Decomposition of the Adducts of Diethylamine and Isopropylamine with Nitrogen(II) Oxide," *Inorganic Chemistry,* 4(3):420–22, 1965.

Reith and Szakali, "Formation and stability of nitric oxide myoglobin I. Studies with model systems," *J. Food Sci.,* 32:188–193 1967.

Reith and Szakali, "Formation and stability of nitric oxide myoglobin I. Studies on meat," *J. Food Sci.,* 32:194–196, 1967.

Riess and LeBlanc, "Preparation of perfluorochemical emulsions for biomedical use: principles, materials and methods", *Blood Substitutes,* Ch. 5, pp. 94–129, 1988.

Riess and LeBlanc, "Solubility and Transport Phenomena in Perfluorochemicals Relevant to Blood Substitution and Other Biomedical Applications", *Pure & Appl. Chem.,* vol. 54, No. 12, pp. 2383–2406, 1982.

Riess, "Highly fluorinate systems for oxygen transport, diagnosis and drug delivery", *Colloids and Surfaces A:Physiochemical and Engineering Aspects,* 84:33–48, 1994.

Riess, "The Design and Development of Improved Fluorocarbon–Based Products for Use in Medicine and Biology", *Art. Cells, Blood Subs., and Immob. Biotech.,* 22(2), pp. 215–234, 1994.

Roberts et al., "Preeclampsia: An endothelial cell disorder," *Am. J. Obstet. Gynecol.,* 161(5):1200–04, 1989.

Saavedra et al., "Secondary Amine/Nitric Oxide Complex Ions, $R_2N[N(O)NO]$, O–Functionalization Chemistry," *J. Org. Chem.,* 57(23):6134–38, 1992.

Sand and Singer, "Stickoxyd und das Grignard'sche Reagens," *In: Justus Liebig's Annalen der Chemie,* C.F. Winter'sche Verlagshandlung, Leipzig, pp. 190–95, 1903.

Schweighardt and Kayhart, European Patent Application No. EP 282,949, filed on Sep. 21, 1988, with U.S. Patent Application No. 28,521, filed on Mar. 20, 1987, *Chem. Abstr.,* 110:199223 and 199180, 1989.

Shukovski and Tsafriri, "The Involvement of Nitric Oxide in the Ovulatory Process in the Rat," *Endocrinology,* 135(5):2287–90, 1994.

Sloviter and Kamimoto, "Erythrocyte Substitute for Perfusion of Brain", *Nature,* vol. 216, pp. 458–460, 1967.

Smith, "Cupferron and Neo–cupferron," G.F. Smith Chem. Co., Columbus, OH, 1938.

Sortino et al., "Involvement of Nitric Oxide in the Regulation of Gonadotropin–Releasing Hormone Release form the GT1–1 Neuronal Cell Line," *Endocrinology,* 134(4):1782–87, 1994.

Stamler et al., "Biochemistry of Nitric Oxide and Its Redox–Activated Forms," *Science,* 258:1898–02, 1992.

Venema et al., "Organization of the bovine gene encoding the endothelial nitric oxide synthase", *Biochimica et Biophysica Acta,* vol. 1218, pp. 413–420, 1994.

Vincent, (Ed.), "Nitric Oxide in the Nervous System", Academic Press, New York, 1995.

Weiner et al., "Induction of calcium dependent nitric oxide synthase by sex hormones", *Proc. Natl. Acad. Sci. USA,* vol. 91, pp. 5212–5216, 1994.

Yalampalli et al., "An L–arginine–nitric oxide–cyclic guanosine monophosphate system exists in uterus and inhibits contractility during pregnancy," *Am. J. Obstet. Gynecol.,* 170(1):175–85, 1994.

Yallampalli and Garfield, "Inhibition of nitric oxide synthesis in rats during pregnancy produces signs similar to those of preeclampsia," *Am. J. Obstet. Gynecol.,* 169(5):1316–20, 1993.

Yallampalli et al., "Nitric Oxide Inhibits Uterine Contractility During Pregnancy But Not During Delivery," *Endocrinology,* 133(4):1899–02, 1993.

Co–pending U.S. Patent Application Serial No. 08/633,337 filed Apr. 17, 1996 (UTSG:181).

Co–pending U.S. Patent Application Serial No. 08/979,281 filed Nov. 26, 1997. (UTSG:219).

FIG. 1

FIG. 2
Time for 50% Healing

FIG. 3

FIG. 4
Time for 50% Healing

SYSTEMS AND METHODS FOR TOPICAL TREATMENT WITH NITRIC OXIDE

BACKGROUND OF THE INVENTION

The present invention relates generally to the fields of tissue malfunction remedies. More particularly, it concerns application of a new nitric oxide-generating mixture to accelerate tissue healing or reduce undesired tissue contractions.

The biological importance of NO is well documented (Lancaster, 1996; Vincent, 1995; Moncada et al., 1992–1994; Feelisch and Stamler, 1996; Williams, 1996; Butler and Williams 1993; Ignarro and Murad, 1995). In mammals, NO is an endogenous physiological mediator of many biological functions. In addition, it is applied pharmacologically in various forms usually referred to as NO donors (nitroglycerin, sodium nitroprusside, etc.) to correct NO deficient states or to regulate the activities of many tissues (see appended list). Topical applications may be used to help wound and burn healing, hair growth, impotence, and cause vasodilatation where needed (e.g., ripening of the cervix in pregnancy). Local higher concentrations of NO (eye, skin, e.g.) are tolerated. Smith et al. (U.S. Pat. No. 5,519,020) describe polymeric nitric oxide sources thought to be useful to promote healing.

Two types of NO synthases (inducible and constitutive) produce NO in living organisms from L-arginine. Synthetic NO donors are also of two different types: those that evolve spontaneously NO as such from chemical precursors (Keefer et al., 1994; Keefer et al., 1993, U.S. Pat. No. 5,212,204; Hansen et al., 1992; Keefer et al., 1996; Garfield et al., 1995, U.S. patent application Ser. No. 08/440,970) or from solutions in suitable solvents (Garfield et al., 1996, U.S. patent application Ser. No. 08/633,337), and those that need metabolic redox processes for releasing NO (usually from higher oxidation states). Among the latter ones, organic nitrates (glycerol trinitrate (trivially known as nitroglycerin), isosorbide dinitrate or organic nitrites have been long used in medicine but they are known to produce tolerance, i.e., the need to progressively increase the dose in order to obtain a constant effect. These are also known to produce undesirable systemic side effects (e.g., headache).

Colorless gaseous NO (under some conditions) may react rapidly with atmospheric oxygen, yielding nitrogen dioxide ($NO_2$), a red-brown gas with much higher toxicity than NO. However, at very low concentrations (up to 0.1 parts per million in air), NO may be administered to humans having breathing problems and have beneficial effects due to its bronchodilatory and vasodilatory activity. The reason why the reaction rate of NO with oxygen is very low at minute concentrations is related to the fact that the square of the NO concentration enters the expression of the reaction rate, according to the stoichiometry (eq. 1):

$$2NO + O_2 \rightarrow 2NO_2 \quad (1)$$

Nitrous acid ($pK_a = 3.37$) is produced from inorganic nitrites on treatment with acids (HA) of higher or comparable strength; in the literature, hydrochloric acid is described for this purpose (Feelisch and Stamler, 1996). Nitrous acid is stable in aqueous solution at low temperature, but it decomposes into NO and $NO_2$ readily at room temperature according to the equations (2) and (3):

$$2HA + 2NaNO_2 \rightarrow 2HNO_2 + 2NaA \quad (2)$$

$$2HNO_2 \rightarrow NO + NO_2 + H_2O \quad (3)$$

There is, under the current U.S. Department of Agriculture regulations, the specification that for curing meat (especially ham and canned meat) and imparting a pink color to it, sodium nitrite must be used in combination with reducing agents such as ascorbate, erythrobate, or α-tocopherol (USDA *Federal Registry*, 1978; Mirvish, *Appl. Pharmacol.*, 1975; Comforth, 1996). Also, the literature specifies that sodium ascorbate has a beneficial effect, again for use in meat products (Reith and Szakali, 1967). It is conjectured that nitric oxide is the active agent in these meat-curing processes, and that the color is due to the binding of nitric oxide to myoglobin. However, the above-mentioned uses antedate considerably the discovery of NO as an important physiological mediator, and until now the methods and procedures selected by the inventors are not described as a means for topical delivery of nitric oxide. Uses and Potential Uses of Nitric Oxide (NO) include Cardiovascular: hypertension; angina; atherosclerosis; preeclampsia (pregnancy induced hypertension; toxemia; eclampsia; HELP syndrome; regulation of vascular conductance; regulation of blood flow; regulation of blood pressure; and myocardial ischemia.

Gastrointestinal: altered motility; and pyloric stenosis.

Lung Function: asthma; treatment of premature babies to increase lung function; and pulmonary hypertension.

Inflammation: autoimmune and immune diseases; acute inflammation; arthritis; resistance to infection; cancer; SLE-Lupus; anaphylactic reactions; and allograft rejection.

Central Nervous System: behavior; epilepsy; Alzheimer's disease; stroke; and growth hormone disorders (e.g., acromegaly).

Pancreas: diabetes.

Female Reproductive System or problems: ovulation; implantation/in vitro fertilization; premenstrual syndrome; dysmenorrhea; uterine contractile disorders; premature labor; cervical dilation; contraception; menopause symptoms; osteoporosis; endocrine disorders; and hormone replacement therapy.

Male Reproductive Problems: impotence; penile erection; male menopause symptoms; endocrine disorders; osteoporosis; and prostate hypertrophy.

Bladder and Kidney Problems: incontinence; renal arterial stenosis; and hypertension.

Dermatological Problems: eczema (skin reaction to foreign particle); autoimmune skin diseases; topical hair loss; acne; wounds; and burns.

The present invention includes formulations and methods for treating many, if not all, of these problems.

SUMMARY OF THE INVENTION

In one important aspect the present invention concerns a method for generating medically applicable nitric oxide. This method comprises combining a nitrite salt, a reductant and a mild acid. The mild acid has sufficient acidity (pKa between about 1 and about 4) to cause degradation of the nitrite to nitric oxide. These components are combined in a diffusion inhibiting medium which controls the rate of nitric oxide release and is sufficiently viscous to topically apply. While ascorbic acid or an ascorbate salt is preferred, other acceptable reductants such as erythrobate or (x-tocopherol, for example, may be used.

Figure 7:
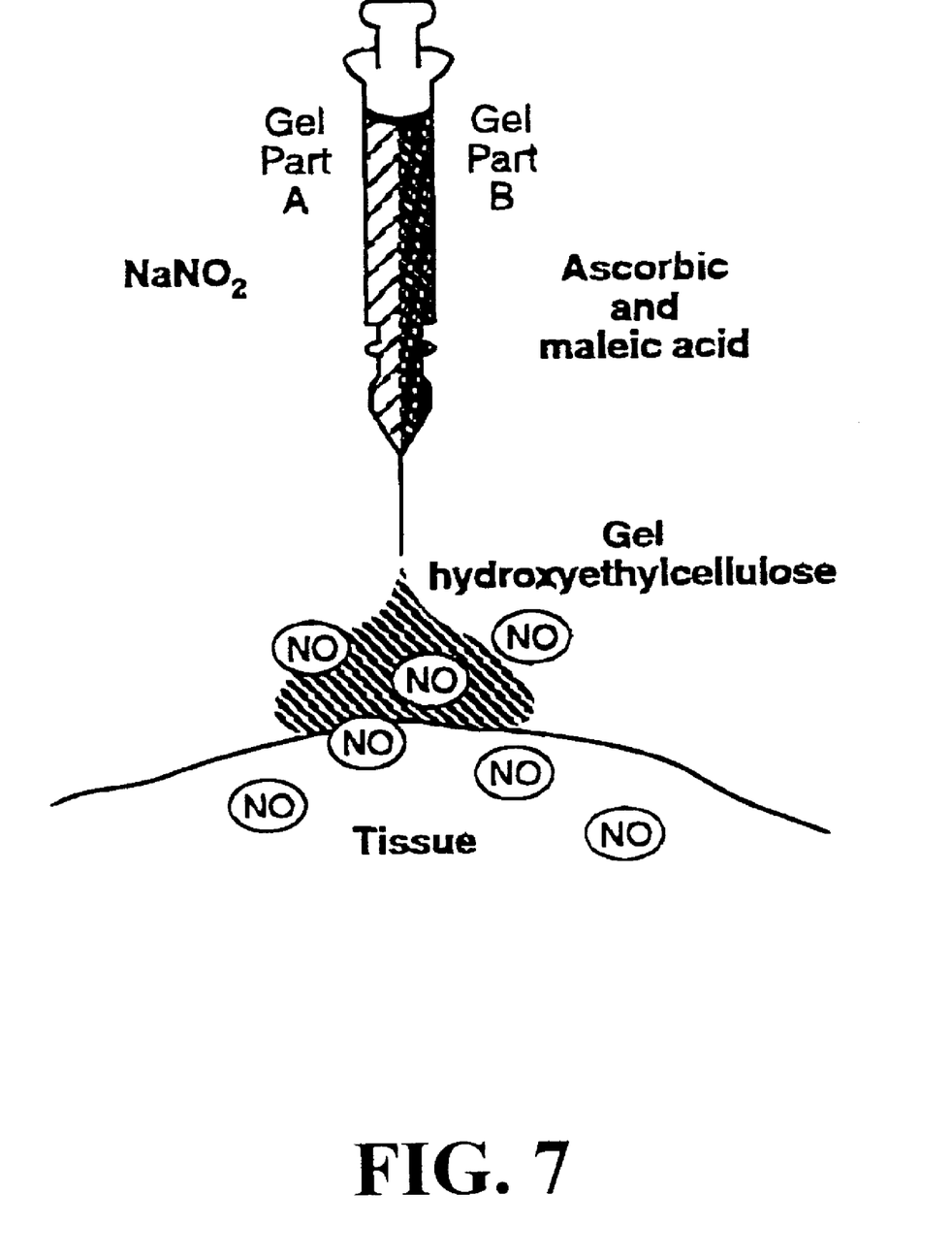
FIG. 7 schematically shows a two ported injection device for administering a nitrite gel and acid gel for mixture and application to a body site.

The present invention, in one important aspect, involves a composition for generating and controlling the release rate of nitric oxide for topical applications that involves more than one gel. In this case, the first aqueous gel comprises a nitrite salt and a second aqueous gel comprises an acid with sufficient acidity to degrade the nitrite salt to nitric oxide. A reductant to help retain the nitric oxide in bioactive form is preferably included in the first or second gel. The acid is preferably an organic acid such as maleic acid, e.g., although inorganic acids such as boric acid, for example may also be suitable. Gellification agents include substances such as hydroxymethyl cellulose, gelatin, agar, and silicic acid, for example. One preferable nitrite salt is sodium nitrite, although others will also be usable. One preferred reductant is ascorbic acid (vitamin C). An acid agent may also be a reductant, such as ascorbic acid or an ascorbic acid variant with a lower pKa, for example. In one aspect, the first and second gels may be combined in layers with the nitrite-containing gel preferably in contact with skin. Prior to application these gels could be separated by an impermeable plastic or metal foil if desired. They could be applied directly to the skin or with an interposed gas-permeable membrane present to avoid possible skin irritation. The aqueous gels may be prepared in isotonic saline solutions and kept sterile prior to use. The topical application includes, of course, application to the skin and may also include any intracavitary application desired. A mixture of powdered sodium nitrite, ascorbic acid, (or other reductant) and maleic acid (or another organic acid of adequate strength) immediately generates nitric oxide (NO) on treatment with water. To slow the NO generation, one may prepare an ointment from a nonaqueous medium (petrolatum, Vaseline, e.g.) and the three powdered ingredients, which, on being applied topically on the skin, will release NO as water permeates through this medium. Alternatively, one may convert the aqueous sodium nitrite solution into an aqueous gel with hydroxyethylcellulose (or other gel-forming substance or compound) and combine this gel with another gel obtained from aqueous ascorbic and maleic acids with hydroxyethylcellulose for topical application (on intact skin, burns, intra-cavity, etc.). The two gels may be admixed immediately before use (possibly from a single container with separate chambers and dual nozzle, via pushing or squeezing the two gels through the nozzle of a device, see e.g., FIG. 7), or may be applied in sandwich-like fashion (possibly as a transdermal patch) for further slowing down the delivery of NO.

In one aspect the present invention involves therapeutically applying NO (nitric oxide) by a method comprising combining a nitrite salt, a biocompatible reductant and an acid with a pK between about 1 and about 4 in a medium and topically applying the combination to a body site. This method for the topical delivery of nitric oxide may be accomplished by steps comprising mixing a powdered nitrite salt with a powdered reductant and an acid having a pKa between about 2 and about 4 in a diffusion-inhibiting, topically applicable medium. The medium is then applied in an effective amount to a desired body site. The diffusion-inhibiting characteristic is a certain measure of viscosity or gellation such that the reaction between the nitrite salt and acid is slowed and controlled for a prolonged release of nitric oxide. Such a medium also is helpful in topical application, for example, to the skin or other body surface. Various nitrite salts may be used, most commonly inorganic ones such as sodium nitrite, although potassium nitrite, calcium nitrite, or any alkali or alkali earth nitrite should be usable. The preferred reductant is one having the reductive capability of preventing or slowing the oxidation of nitric oxide to nitrous oxide. Preferred reductants include ascorbic acid tocopherol, ascorbate salts, erythrobates or alpha-tocopherol. Other acceptable reductants are well known to those of skill in the arts. Sometimes the acid, particularly if it is an organic acid, may also be a reductant. Ascorbic acid, although slightly weaker an acid than desired for optimal nitric oxide release and control, does have reductive characteristics and may be used under some circumstances as being both a reductant and an acid. Maleic acid is one preferred organic acid which is acceptable. Inorganic acids with the appropriate pKs should be acceptable, particularly if they are biologically acceptable (e.g., boric acid). The medium for dissolution of a nitrite and acid and/or reductant may be an aqueous medium or, in fact, a nonaqueous medium. Aqueous media are generally preferred and readily prepared as gels, although organic salves may also be usable under some circumstances. Methods for the application of these materials to a desired area are manifold, some of which are mentioned here and include applying a nitrite-containing gel or salve layer to the skin or other body site. This would be followed by overlaying a layer of acid and/or reductant. This should give rise to a controlled rate of nitric oxide release to contact the desired bodily surface. These can be manually applied or can be applied as premeasured layers. In some cases the gels may simply be mixed just prior to application to form a relative homogeneous but diffusion-inhibiting salve or gel with all components mixed therein and a sufficiently slow and controlled rate of nitric oxide generation.

Aqueous gelling agents usable in the methods of the present invention include agars, hydroxyethyl celluloses and many other materials known to those of skill in the art usable in preparing aqueous-based gels. The appropriate gels may be prepared in advance and packaged separated by an impermeable plastic or metal layer, meant to be removed just before use. After removal the layers may be topically applied, the nitrite-containing layer being preferably applied closest to the body site. In some cases, it may be desirable to interpose a gas permeable membrane on the body site prior to the application of the gel or ointment nitric oxide source. This may lessen any skin irritation possibly resulting with certain individuals.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention comprises a simple procedure for generating nitric oxide (NO) from water or biological fluids and a mixture of powdered biocompatible solid reagents, and also for converting aqueous solutions of such reagents into ointments or gels for topical application and slow delivery of NO. However, with reducing agents, only NO is produced, this constituting one of the main aspects of the present invention.

Biocompatible systems and procedures for generating nitric oxide (NO) are described herein that are particularly useful for topical applications.

Ascorbic acid (vitamin C) is one preferred biocompatible reducing agent for nitrites; its $pK_a$ is 4.10, making it a slightly weaker acid than nitrous acid. An acid with a pKa between about 1 and about 4 is preferred for NO generation, maleic acid being particularly preferred. Maleic acid ($pK_a$= 1.83 for the first ionization step) is about 30 times stronger than nitrous acid, is a crystalline solid without water of crystallization, and its salts are also tolerated biologically; many medicinal drugs with aliphatic amino groups are administered as maleates.

The methods described herein include mixing an aqueous solution of sodium nitrite with an aqueous solution of an equimolar amount of maleic acid, in the presence of an excess of ascorbic acid. The sodium nitrite is preferably kept separately from the other two ingredients because even ascorbic acid alone slowly generates NO if admixed with sodium nitrite. originality and advantages of the present procedure in one preferred embodiment include employing three safe and inexpensive compounds with convenient characteristics for producing NO free of any other residue that may cause adverse biological effects (as is potentially the case of many newly synthesized NO donors), and also free from the need of enzymatic reactions that may lead to tolerance (as is the case of organic nitrates functioning as NO donors). The composition of the mixture selected by the inventors is inventive, because so far no composition has been marketed or used that consists of (i) a nitrite salt with (ii) an organic acid of adequate strength and (iii) a reducing agent, all three ingredients being biocompatible. Few organic or other acids of the necessary strength are biologically tolerated, and in the absence of a reducing agent such as ascorbic acid the deleterious nitrogen dioxide could also be produced along with NO, as seen in eq. (3). One may therefore assert that the method and procedure described herein are unique in terms of the necessity of having the three types of ingredients selected by the inventors, and among representatives of these types the inventors have selected preferred ones.

A two gel method for delivery of NO will have the following properties. Dosage (total) can be controlled simply by adjusting the quantity of nitrite and acid. Rate can be independently controlled by adjusting the viscosity of the gel. Thus, a high total dosage can be delivered over a long period of time or a low total dosage can be delivered rapidly, as desired. In addition, various physical means for applying successive doses can be easily developed. For example, multilayer sandwiches could be formed with each successive layer activated by removing sequential barriers between gels (which themselves could even be of different strengths). Thus, a wound could remain covered for several treatments.

Another feature of the gels is that they are compatible with the addition of various agents such as sterilizing compounds and antibiotics, e.g.

Other mechanisms of application (other than topical) are possible. This technoligy might be used as sprays, suppositories, (aural, nasal, vaginal or rectal) or even injectable form to control many biological functions. It might also be dispensed in dropper form to be used in the eye, ear, nose or throat. Almost all these applications deal with treatment of inflammation. The IV applications might be useful for acute angina and to regulate the cardiovascular system.

The gel might also be used in combination with various agents including antibiotics, anesthetics, analgesics, anti-inflammatory agents such as corticosteroids and nonsteroidal anti-inflammatory agents, antiviral agents, vasodilators or vaso constrictors, sunscreen preparations (PABA), antihistamines, other hormons, such as estrogens, progesterone, androgens, antiseborretic agents, other cardiovascular agents, mast cell stabilizers, scabicides or pediculicides, keratolytics, lubricants, narcotics, shampoos, acne preparations, antiseborrheic agents, burn preparations, cleansing agents, deodorants, depigmenting agents, diaper rash products, emollients and moisturizers, photosensitizing agents, poison ivy or poison oak or sumac proudcts, sunburn preparations, tar-containing preparations, wart preparations, wet dressings and wound care products. This would reduce any potential danger of infection introduced by the process.

The present gel technology is preferably but not necessarily a local NO delivery system as opposed to a systemic one. Therefore, the many systemic side effects of other NO treatments (such as nitroglycerin) should be completely avoided. This is an important advantage for a variety of problems.

A further advantage of the local application of the gels is that it is self regulating in the sense that when the desired effect of the treatment has been achieved, the remaining amount can simply be wiped off and the release stops. For subjects who might have some allergic response to other treatments, this ability to immediately stop treatment should be beneficial.

In addition to the list of uses and potential uses of NO, four important specific applications of the gel technology are worthy of more detailed discussion. These are generally related to the fact that the gels produce NO locally which in turn enhances local circulatory response.

1. Since topical application of the gels has been shown to immediately enhance local blood flow, the gel technology can have important uses in treatments of male reproductive problems, especially penile erection and impotence. The ability to control dosage directly may be important here. Of course, if desired, antibiotics, spermacides and/or other additives may be included in such a gel.

2. Enhancement of local circulation is important for hair replacement and growth. The gel technology can be used to treat topical hair loss, particularly insofar as the hair loss is at least partially caused by microcirculation defects.

3. Burns respond to treatment with the gel as demonstrated in animal models the results of which are included herein. Use of the gel technology in conjunction with other compounds may have application to even minor bums such as sunburn and other wounds.

4. NO donor compounds are important in the control of cervical dilation. The gel technology for this purpose is particularly appealing. First, it can be controlled directly and second, it is purely local as opposed to systemic.

There are numerous types of compounds which might be added to gels without unfavorably altering the NO donation properties but which would have some added features already known. These include antibiotics, steroids, antihistamines, antiinfective agents, prostaglandins, antipyretics, analgesics, anticycotics, antiseborrheic agents, anti psoriasis agents, antipruritics and local anesthetics. Also they may be combined with locally acting cardiovascular agents, e.g., alpha or beta blockers and Rogaine. Another type of compound which might be added to the gels is vasomax or other penile erectile agents. One can also combine the gels with vitamins, skin softeners, emolients, clearing agents, enzymes and keratolytics.

The following examples are included to demonstrate preferred embodiments of the invention. It should be appreciated by those of skill in the art that the techniques disclosed in the examples which follow represent techniques discto function well in the pto function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Experimental procedure for checking the rapid release of NO.

Immediately before use a powdered combination of sodium nitrite (15 mmoles) and ascorbic acid (20 mmoles) is mixed magnetically with powdered maleic acid (20 mmoles) in a 500 ml four-necked flask connected (via ground-glass joints having stopcocks) to a vacuum pump, a manometer, an argon inlet, and a stoppered dropping funnel with pressure equalizer. After repeated evacuations and purgings with argon, water from the dropping funnel is admitted into the flask with stirring. A quantitative evolution of colorless NO with effervescence is observed by the pressure increase and corresponds to 15 mmoles of NO. On admitting air into the flask until the pressure equalizes with atmospheric pressure, the red-brown color of $NO_2$ appears. The chemical reaction (4), where vitamin C is $Asc(OH)_2$ and maleic acid as MalH shows the reaction producing NO:

$$2NaNO_2+2MalH+Asc(OH)_2 \rightarrow 2NO+2NaMal+2H_2O+AscO_2 \quad (4)$$

EXAMPLE 2

Experimental procedure for preparing an ointment which will slowly release NO.

The three components mentioned above, in the same ratios, are admixed with a petroleum-based nonaqueous ointment such as petrolatum or Vaseline, forming a thick slurry. When applied topically on the skin, this ointment will slowly release NO with water vapor that permeates through the nonaqueous medium.

EXAMPLE 3

Experimental procedure for preparing a water-based gel for gradual topical release of NO.

The three components of Example 1 are used, but sodium nitrite and maleic acid are kept in separate gels prior to use. A warm solution of sodium nitrite (0.1 mole (1 to 5% concentration) in distilled water is converted into a gel by adding hydroxyethylcellulose (molecular weight 250,000–1, 250,000) or another gel-forming substance such as another cellulose derivative, gelatin or agar, e.g., in such a ratio as to obtain the desired consistency of the gel, and to incorporate all the solution, after 24 h at room temperature. For instance, with 1.6 g of hydroxyethylcellulose with average molecular weight 750,000, one obtains a satisfactory transparent gel with 50 ml solution.

Separately, another gel is prepared similarly from distilled water, hydroxyethylcellulose, maleic acid (0.1 moles) and ascorbic acid (0.15–0.2 moles, same concentration as the nitrite). On admixing equal amounts of the two gels immediately before use, placing the mixture on intact skin, and covering it (or not) with an adhesive bandage, NO will be delivered topically. It is preferable (when mixing the two gels is not done or is done on the skin) to have the gel with nitrite in contact with the skin, and to apply the other gel over it, in order to reduce any irritation due to the low pH of the mixture or acid gel. If the two gels have sufficiently high consistency, thin slices of appropriate dimensions from each of the two gels can be cut and sandwiched, separated by an impermeable plastic or metal foil; immediately before use the foil can be removed, the two slices can be slightly pressed against one another and covered by the air-tight adhesive bandage, if desired, for gradual topical delivery of NO.

In all cases, care should be exercised in order to minimize or avoid any overdosage of NO or of nitrite. Contact between the atmosphere and the mixture producing nitric oxide is preferably avoided or minimized because, under some conditions, NO may be rapidly oxidized by air (unless extremely diluted) to afford undesirable nitrogen dioxide.

EXAMPLE 4

Wound Healing—Nitrite Reduction/aloe

Objective: To investigate the effects of Nitric Oxide on a second degree partial thickness burn. Also, to compare the healing rate of NO treatment with that of Aloe vera. The study will include different gels with different concentrations and viscosities.

FIGS. 1–6 present the data from two separate experiments. Both experiments deal with healing of second degree burns on rats as a function of time and treatment methodology.

In both experiments, Sprague Dawley male rats (average weight 275 grams) were anesthetized with 0.025 ml of sodium nebutal. Once under anesthesia, the rats' backs were shaved as close as possible, followed by a treatment of NARE for five minutes to remove any remaining hair.

A rubber pad template with a removed oval section in the center was used to standardize the burn size among the animals. This template was placed over a bath containing 75 degree Celsius water, allowing only a small area of hot water surface area.

The anesthetized animal's backs were then pressed against the template for 10 seconds, only being burned by the oval opening. The animals were treated with various applications immediately after being burned. The animals were next allowed to awaken on a heating pad and returned to their cages. In general, wound size increases initially regardless of treatment methodology, as damaged skin sloughs off.

Measurement of wound areas was done directly by tracing the wound on transparent film every two days with areas measured via planimetry. In each experiment, groups of 5 rats were utilized. Thus, the first experiment, with five different groups, was for a total of 25 animals. In the second experiment with nine groups, a total of 45 animals were involved.

The first experiment demonstrating the healing effect of the gel technology utilized the following gels.

$NaNO_2$ Gel: Dissolve 3g $NaNO_2$ in 200 ml distilled water (some heat required). Upon dissolution, add 1.5 grams of hydroxyethyl cellulose gel (MW 720,000).

Acid Gel: Dissolve 7 grams of Vitamin C and 3.3g Maleic acid in 200 ml distilled water. Upon dissolution, add 1.5 grams of hydroxyethyl cellulose (MW 720,000) was dissolved.

Figure 1:
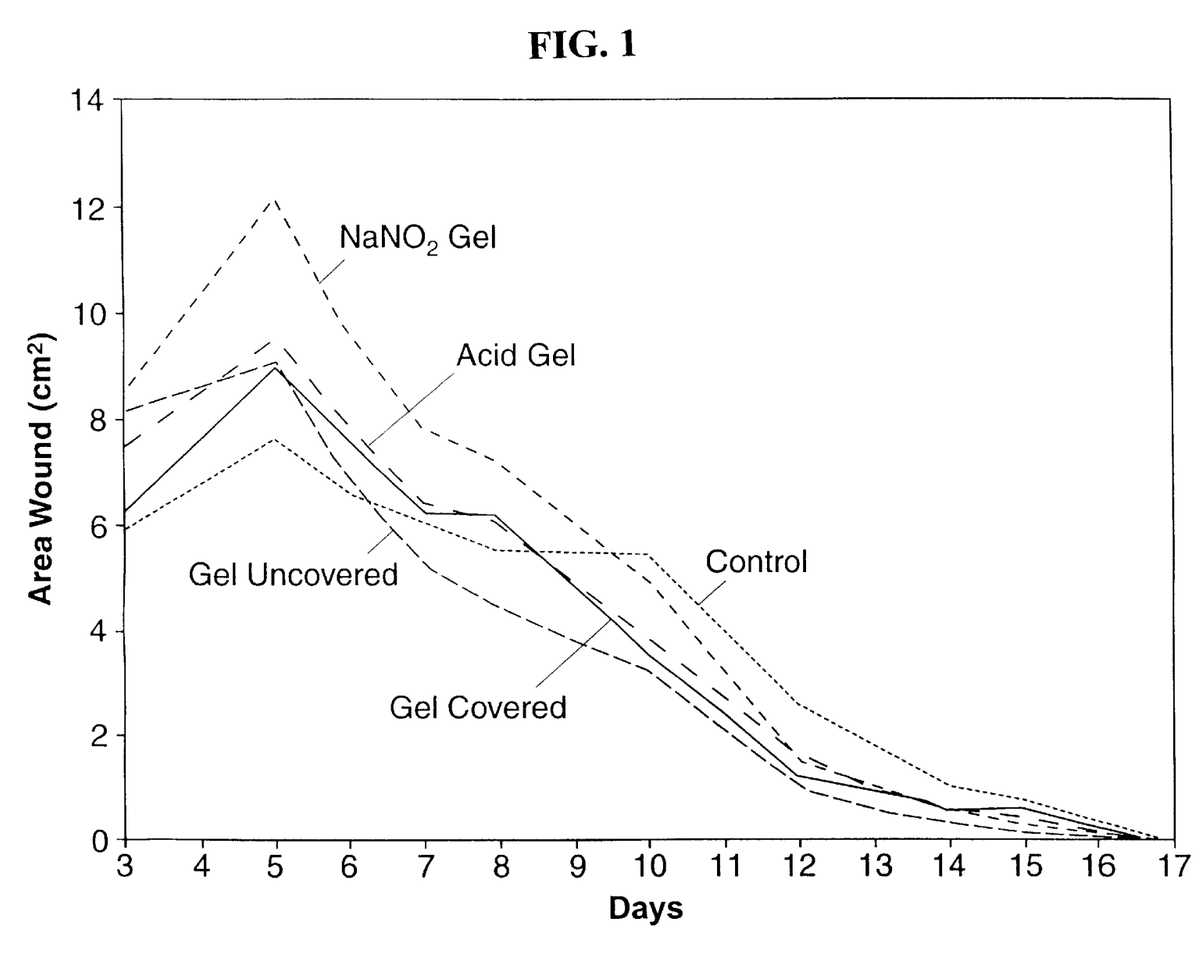
FIG. 1 gives the raw data for healing of second degree burns comparing control with covered and uncovered mixed gels (which release NO) and the individual acid or nitrite gels.
Figure 2:
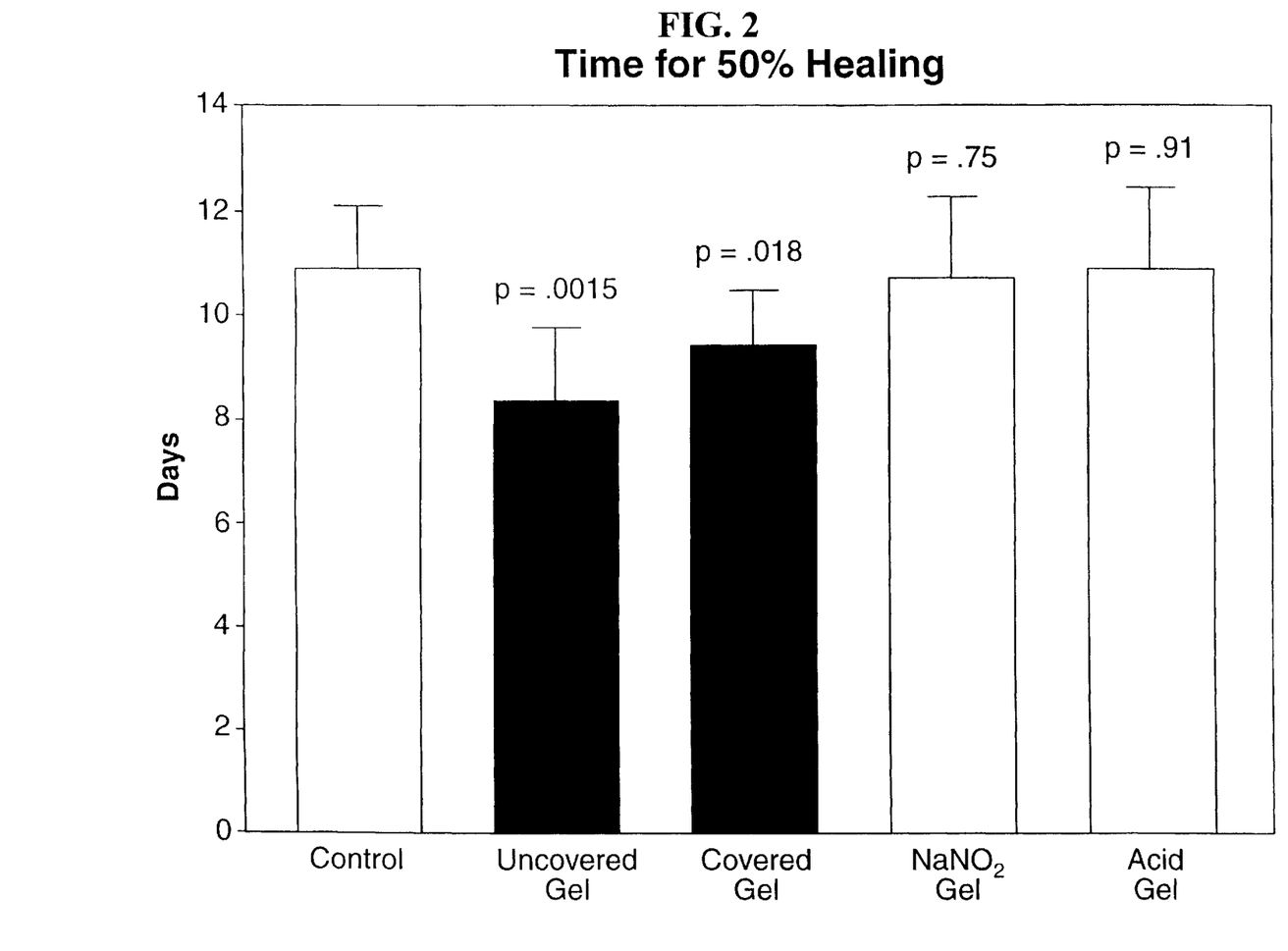
FIG. 2 compares the time to 50% healing from the initial wound size for the experiment of FIG. 1. The error bars and p-values are given. The uncovered gel is statistically shown to be superior to all other methods, with high statistical certainty.
Figure 5:
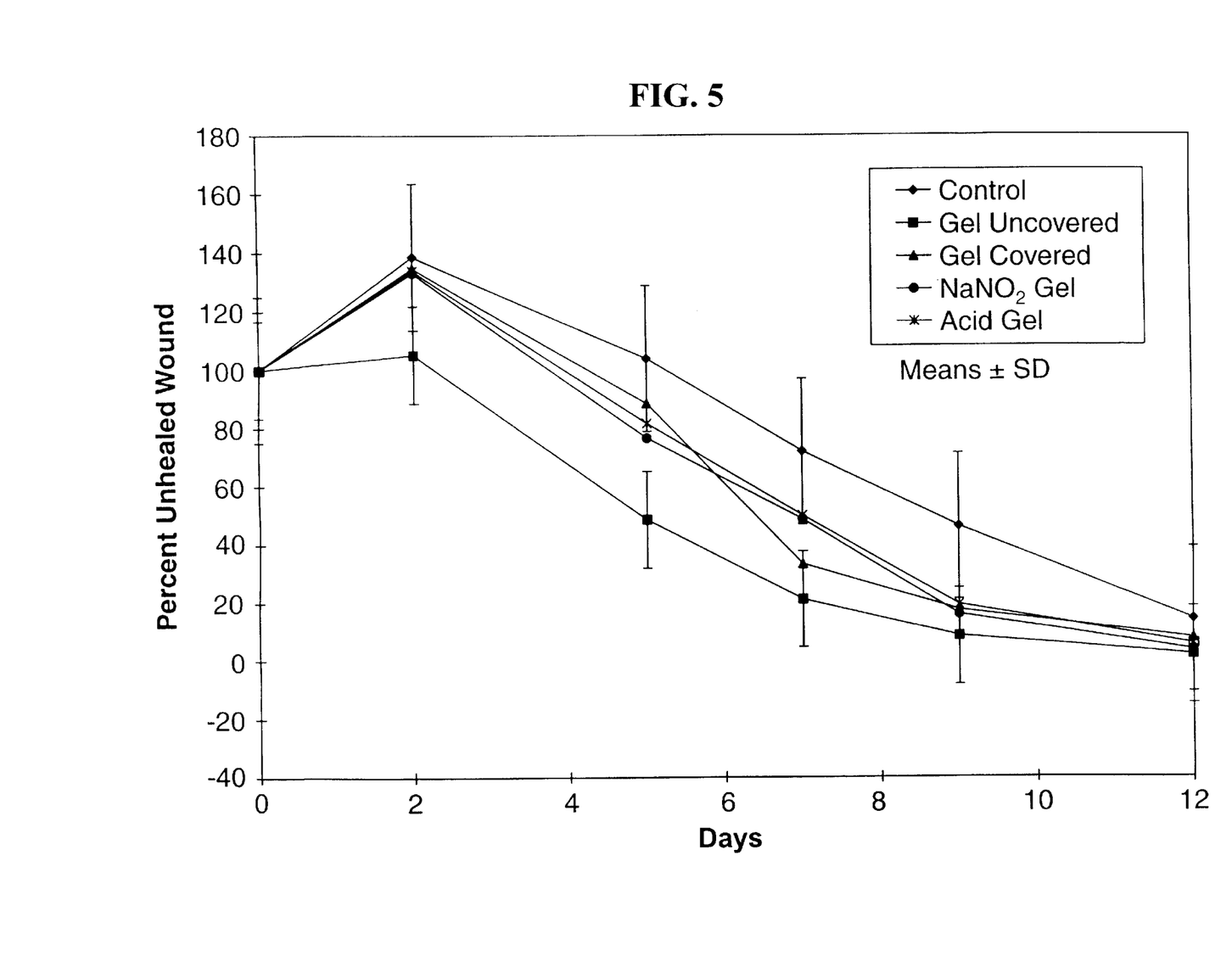
FIG. 5 is for the same experiment as FIGS. 1 and 2 but showing a normalized curve where each wound is normalized to one and the ordinate is the percent remaining unhealed.

The results from the first experiment are shown in FIGS. 1, 2 and 5.

The second experiment investigated modifications of the gels to higher sodium nitrite concentration and higher viscosity compared to the first experiment and also compared healing to Aloe Vera treatments (Dermaide Aloe Cream, Dermaide Research Corp., Ill.). The second experiment also compared treatment frequencies—once (1x) as compared to twice (2x) per day.

To obtain the double viscosity gels, a higher molecular weight hydroxyethyl cellulose (MW 1,300,000) was substituted. To obtain the double nitrite concentration, the $NaNO_2$ concentration was doubled in the sodium nitrite gel (i.e. use 6 g instead of 3).

Figure 3:
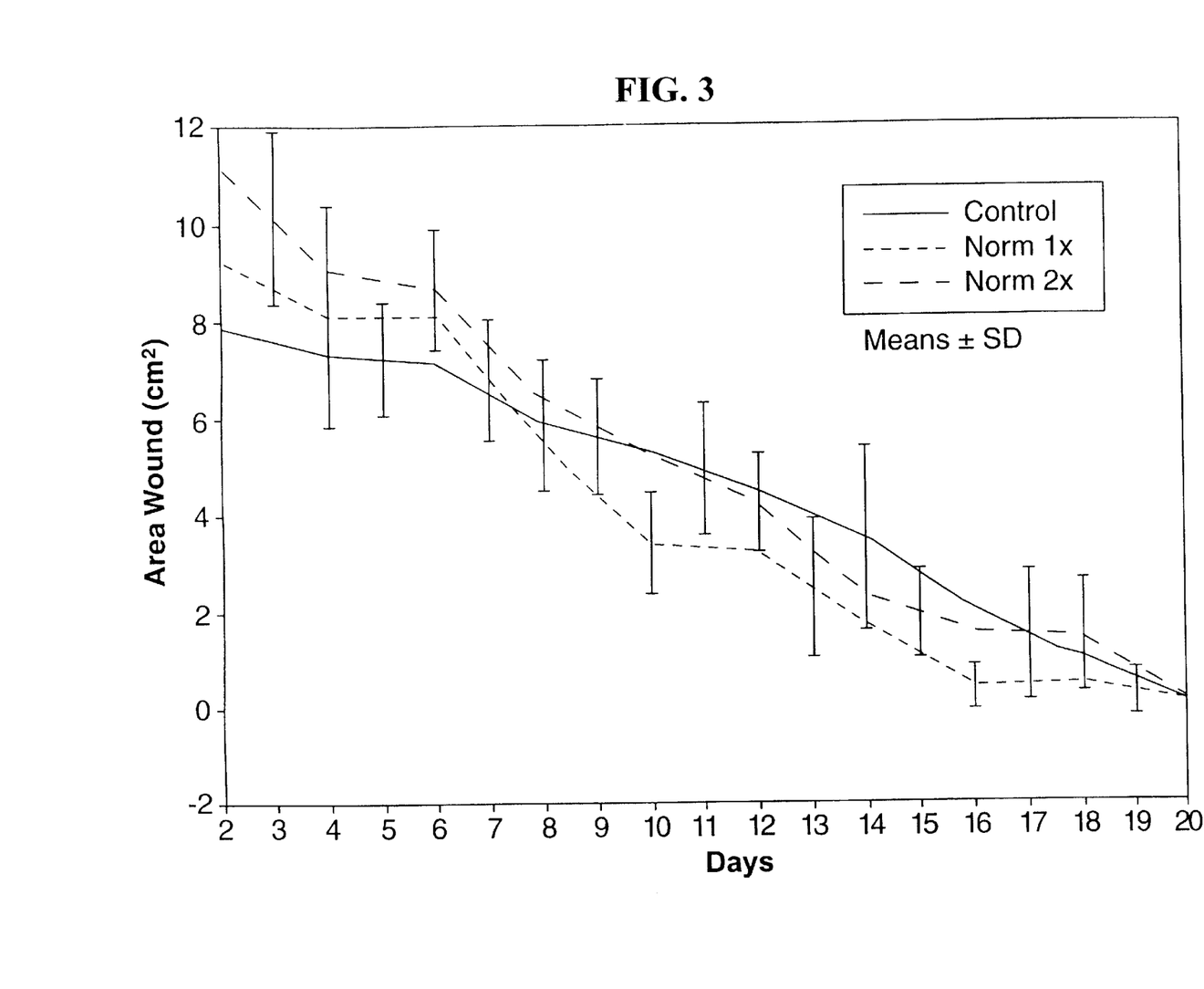
FIG. 3 compares gels releasing NO applied once or twice daily.
Figure 4:
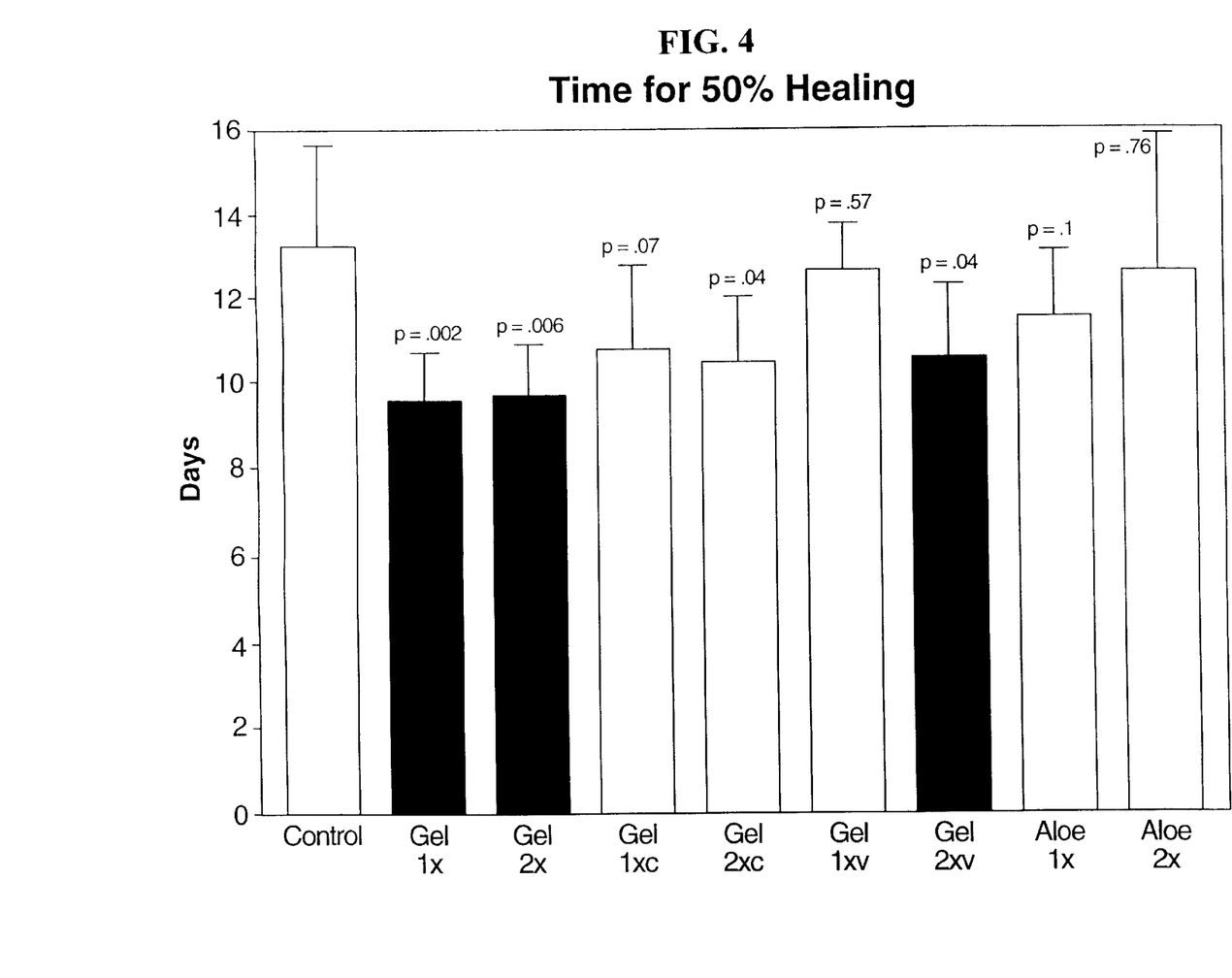
FIG. 4 is as described for FIG. 3 but comparing higher viscosity gels, higher nitrite concentration gels and aloe vera cream. Again, statistical significance is found favoring the gels. The legend means: control, gel treatment once (1x) per day, gel twice (2x) per day, regular (1XC) or concentrated (2XC) nitrite gel once per day, a normal nitrite concentration (1XV) or more viscous gel (2XV) per day, and finally aloe vera at two viscosities.
Figure 6:
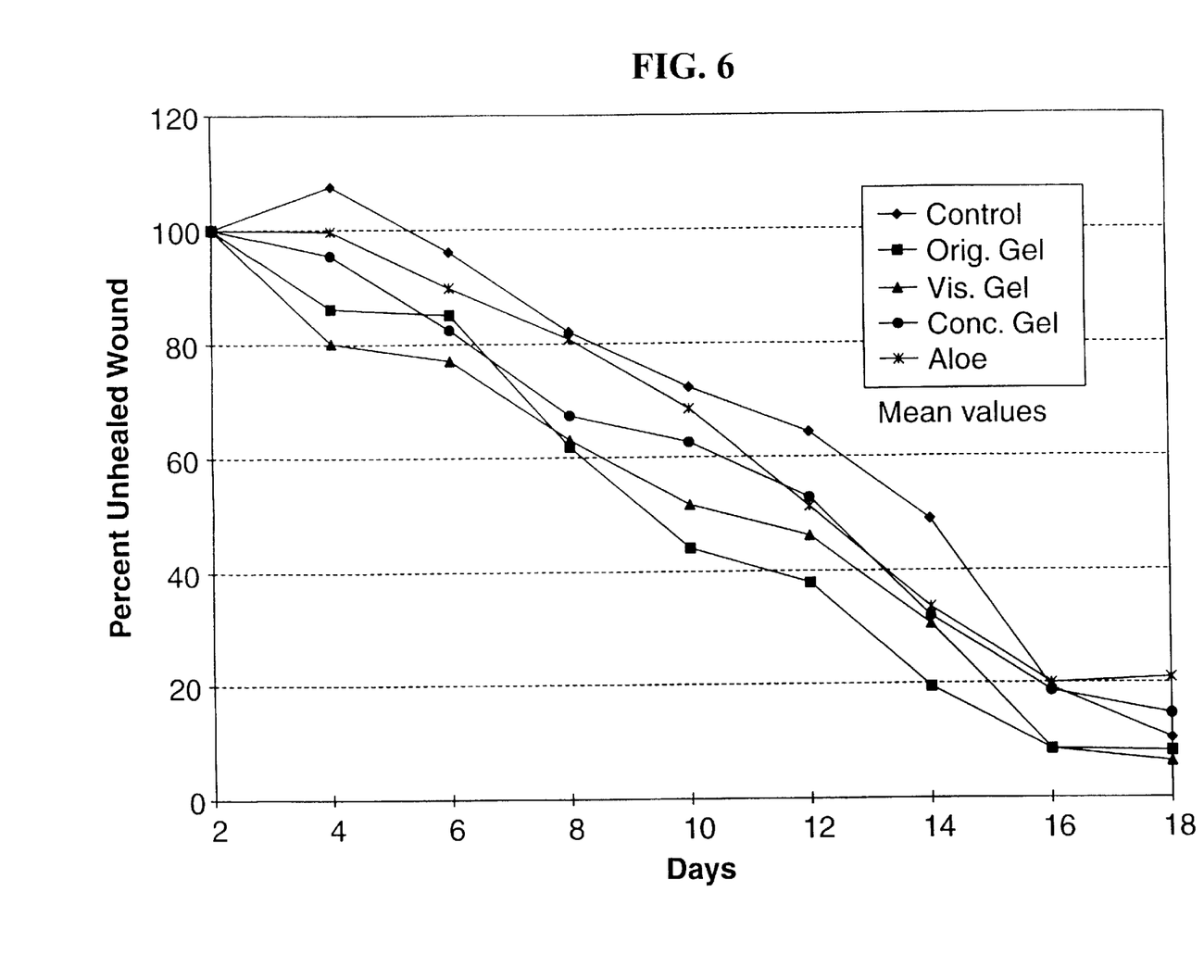
FIG. 6 is a normalized curve for the experiment in FIGS. 3 and 4.

The results from the second experiment are shown in FIGS. 3, 4 and 6. In all cases, the gels are preferably sealed after forming.

FIG. 1 gives the raw data for healing of second degree burns comparing control with covered and uncovered mixed gels (which release NO) and the individual acid or nitrite gels. The result demonstrates that healing efficacy is the result of the NO released as opposed to the components in the individual gels. The uncovered and covered gels which release NO clearly heal faster in absolute terms.

FIG. 2 compares the time to ½ healing from the initial wound size for the first experiment. The error bars and p-values are given. The uncovered acid-nitrite gel is statistically shown to be superior to all other methods with high statistical certainty (followed by the covered acid-nitrite gel).

FIG. 3 compares once and twice daily gel applications. Both applications caused more rapid healing than controls.

FIG. 4 shows healing ½ time but this time comparing higher viscosity gels, higher nitrite concentration gels and aloe vera creams. Again, statistical significance is found favoring the No producing gels. The legend means: control, gel treatment once (1x) per day, gel twice (2x) per day, nitrite concentration gel (1XC) and twice concentrated (2XC), a normal nitrite concentration but normally viscous gel (1XV) and more viscous gel (2XV) once per day, and finally aloe vera once or twice per day.

FIG. 5 is for the same experiment as FIGS. 1 and 2 but showing a normalized curve where each wound is normalized to one and the ordinate is the percent remaining unhealed.

FIG. 6 is a normalized curve for experiment two shown in FIGS. 3 and 4.

EXAMPLE 5

Note on biological tests to date.

These tests indicate efficacy of gel treatments for wound healing. This is, however, just one of the applications of the technology. The present invention demonstrates that the systems described herein release NO, and also that they produce increased local blood flow. That observation is independent of these burn experiments and certainly makes the discovery applicable in any case where increased local blood circulation can be therapeutic.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Butler and Williams, *Chem. Soc. Revs.,* 22:233, 1993

Cornforth, In: *Nitric Oxide. Principles and Actions,* Ed. J. Lancaster Jr., Academic Press, San Diego, p. 259, 1996.

Feelisch and Stamler, (Eds.), "Methods in Nitric Oxide Research," Wiley, New York, 1996

Feelisch and Stamler, In: *Methods in Nitric Oxide Research,* Eds. M. Feelisch and J. S. Stamler, Wiley, p. 71, namely p. 102, 1996.

Garfield, Balaban, Seitz, Klein, Lesko, U.S. patent application Ser. No. 08/440,970, May 15, 1995.

Garfield, Balaban, Seitz, U.S. patent application Ser. No. 08/633,337, Apr. 17, 1996.

Hansen, Croisy, Keefer, In: *N-Nitroso Compounds: Occurrence and Biological Effects* (Eds. Bartsch, H., O'Neill, I. K., Castegnaro, M. and Okada, M.), International Agency for Research on Cancer Publication No. 41, Lyon, p. 21, 1992

Ignarro and Murad, (Eds.), "Nitric Oxide. Biochemistry, Molecular Biology, and Therapeutic Implications", *Advances in Pharmacology,* Academic Press, San Diego, 1995.

Keefer, Christodolou, Dunams, Hrabie, Maragos, Saavedra, Wink, In: *Nitrosamines and Related N-Nitroso Compounds: Chemistry and Biochemistry,* (Eds. R. N. Loeppky and C. J. Michedja), ACS Symp. Series No. 553, Amer. Chem. Soc., Washington, D.C., p. 136–146, 1994

Keefer, Nims, Davies, Wink, D. A., *Methods in Enzymology,* 268:281, 1996.

Keefer, Wink, Dunams, Hrabie, U.S. Pat. No. 5,212,204 (May 18, 1993); *Chem. Abstr,* 113:145344, 1990 for patent application Ser. No. 423,279 (Mar. 1, 1990)

Lancaster, (Ed.), "Nitric Oxide. Principles and Actions", Academic Press, New York, 1996

Mirvish, *Appl. Pharmacol.,* 31:325, 1975.

Moncada, Marletta, Hibbs, Feelisch, Busse, (Eds.), "The Biology of Nitric Oxide", vols. 1–4, Portland Press, Colchester, 1992–1994

Reith and Szakali, *J. Food Sci.,* 32:188, 194, 1967.

Smith et al.,(U.S. Pat. No. 5,519,020), issued May 21, 1996.

USDA *Federal Registry*, Washington, D.C., 43:20992, 1978.
Vincent, (Ed.), "Nitric Oxide in the Nervous System", Academic Press, New York, 1995
Williams, *Chem. Soc. Revs.*, 25:77–84, 1996

What is claimed is:

1. A method for therapeutically applying NO, the method comprising topically applying first gel comprising a nitrite salt, and a biocompatible reductant and a second gel comprising an acid with a pKa between about 1 and about 4 to a body site in an amount effective to enhance local blood flow.

2. A method for topical delivery of nitric oxide (NO) comprising applying an effective amount of a first gel comprising a nitrite salt, and a second gel comprising a biocompatible reductant, and an acid having a pKa between about 1 and about 4 to a body site.

3. The method of claim 1 or 2 where the reductant is an ascorbate salt, an erythrobate or α-tocopherol.

4. The method of claim 1 or 2 where the reductant is ascorbic acid.

5. The method of claim 1 or 2 where thewhere the acid is an organic acid.

6. The method of claim 1 or 2 where the acid is maleic acid.

7. The method of claim 1 or 2 where the acid is an inorganic acid.

8. The method of claim 1 or 2 where the nitrite salt is an inorganic salt.

9. The method of claim 1 or 2 where the nitrite salt is sodium nitrite.

10. The method of claim 1 or 2 where the gels are aqueous gels.

11. The method of claim 1 or 2 where the body site is a burn.

12. A composition for generating and controlling the release rate of NO for topical applications, the composition comprising a first aqueous gel and a second aqueous gel, the first gel comprising a nitrite salt, and the second gel comprising an acid having a pKa between about 1 and about 4 and at least one of the first and second gel comprising biocompatible reductant.

13. The composition of claim 12 where the reductant is ascorbic acid, an ascorbate salt, an erythrobate or α-tocopherol.

14. The composition of claim 12 where the reductant is ascorbic acid.

15. The composition of claim 12 where the acid is an organic acid.

16. The composition of claim 12 where the acid is maleic acid.

17. The composition of claim 12 where the acid is an inorganic acid.

18. The composition of claim 12 where the nitrite salt is an inorganic salt.

19. The composition of claim 12 where the nitrite salt is sodium nitrite.

* * * * *